United States Patent [19]

Wang et al.

[11] 4,221,967
[45] Sep. 9, 1980

[54] GAMMA RAY CAMERA

[75] Inventors: Shih-Ping Wang, Los Altos; Charles D. Robbins, Los Altos Hills, both of Calif.

[73] Assignee: Diagnostic Information, Inc., Sunnyvale, Calif.

[21] Appl. No.: 885,169

[22] Filed: Mar. 10, 1978

[51] Int. Cl.² .......................... G01T 1/20; H01J 31/50
[52] U.S. Cl. .......................... 250/363 S; 250/213 VT; 250/367
[58] Field of Search ............... 250/361, 366, 213 VT, 250/363 S, 367; 313/94

[56] References Cited

U.S. PATENT DOCUMENTS

| | | | |
|---|---|---|---|
| 2,739,258 | 3/1956 | Sheldon | 250/367 |
| 3,011,057 | 11/1961 | Anger | 250/363 S |
| 3,531,651 | 9/1970 | Lieber | 250/213 VT |
| 3,558,893 | 1/1971 | Ball | 250/213 VT |
| 3,683,180 | 8/1972 | Martone et al. | 250/363 S |
| 3,683,185 | 8/1972 | Muehllehner | 250/213 VT |
| 3,723,734 | 3/1973 | Loveday | 250/367 |
| 3,829,688 | 8/1974 | Barrett | 250/320 |
| 3,838,273 | 9/1974 | Cusano | 250/213 VT |
| 3,911,278 | 10/1975 | Stout | 250/369 |
| 4,104,516 | 8/1978 | Wang et al. | 250/213 VT |

FOREIGN PATENT DOCUMENTS 1120393  7/1968  United Kingdom ..................... 250/366

OTHER PUBLICATIONS

Conrad et al., "The Scinticon, A New Gamma Camera", Electromediea, 4, 5/1973, pp. 220-225.

Primary Examiner—Alfred E. Smith
Assistant Examiner—Carolyn E. Fields
Attorney, Agent, or Firm—Limbach, Limbach & Sutton

[57] ABSTRACT

An Anger gamma ray Camera is improved by the substitution of a gamma ray sensitive, proximity type image intensifier tube for the scintillator screen in the Anger camera, the image intensifier tube having a negatively charged flat scintillator screen and a flat photocathode layer and a grounded, flat output phosphor display screen all of the same dimension (unity image magnification) and all within a grounded metallic tube envelope and having a metallic, inwardly concaved input window between the scintillator screen and the collimator.

21 Claims, 10 Drawing Figures

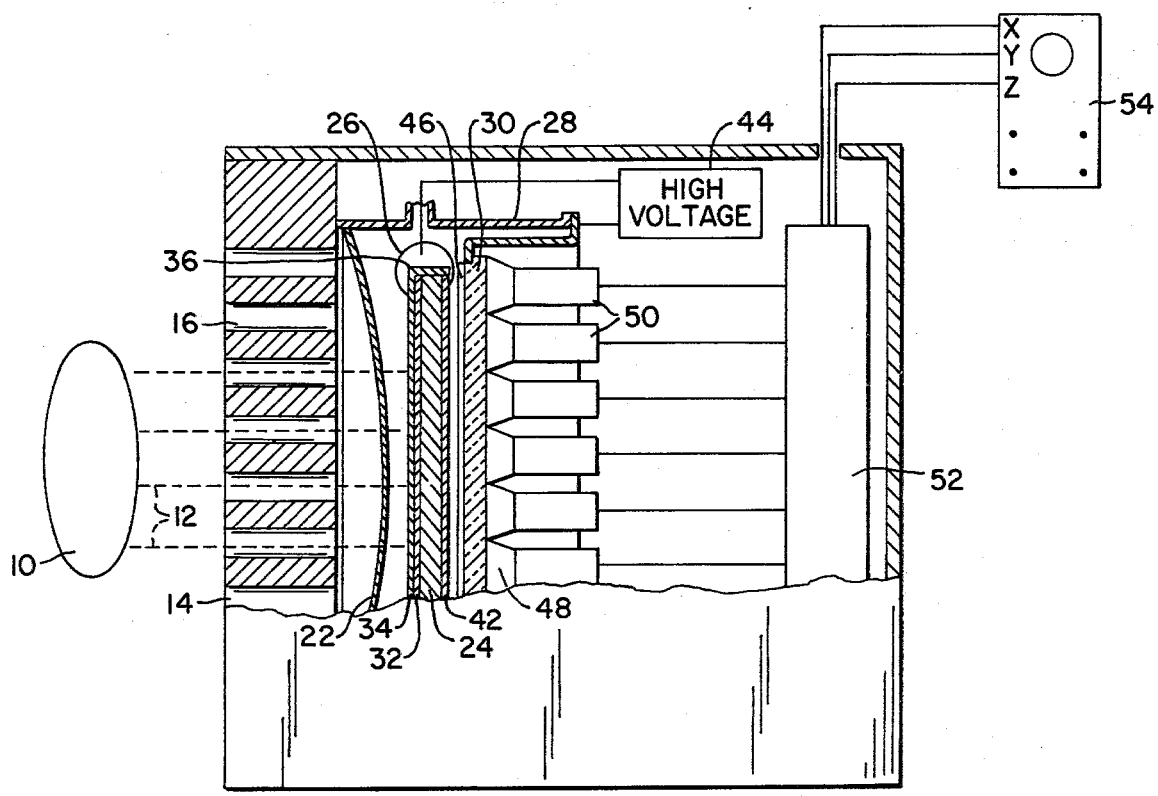
FIG._1.
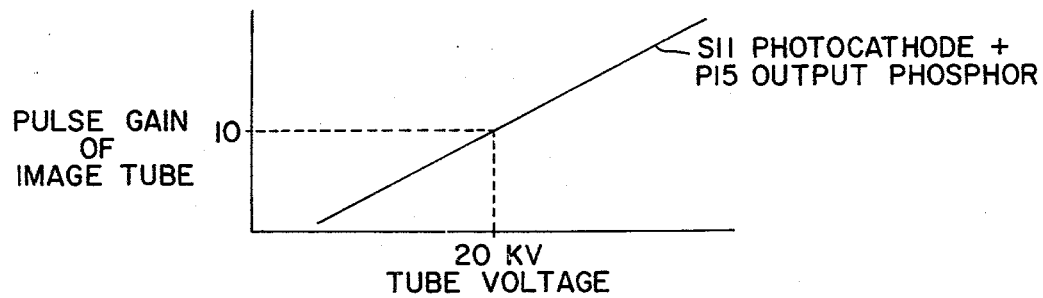
FIG._2.
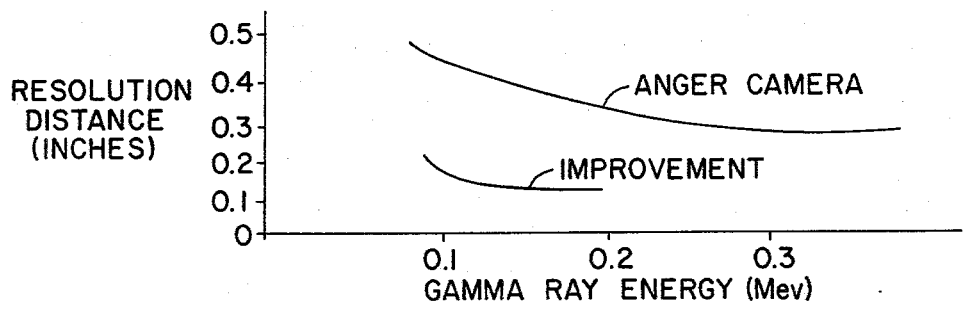
FIG._3.

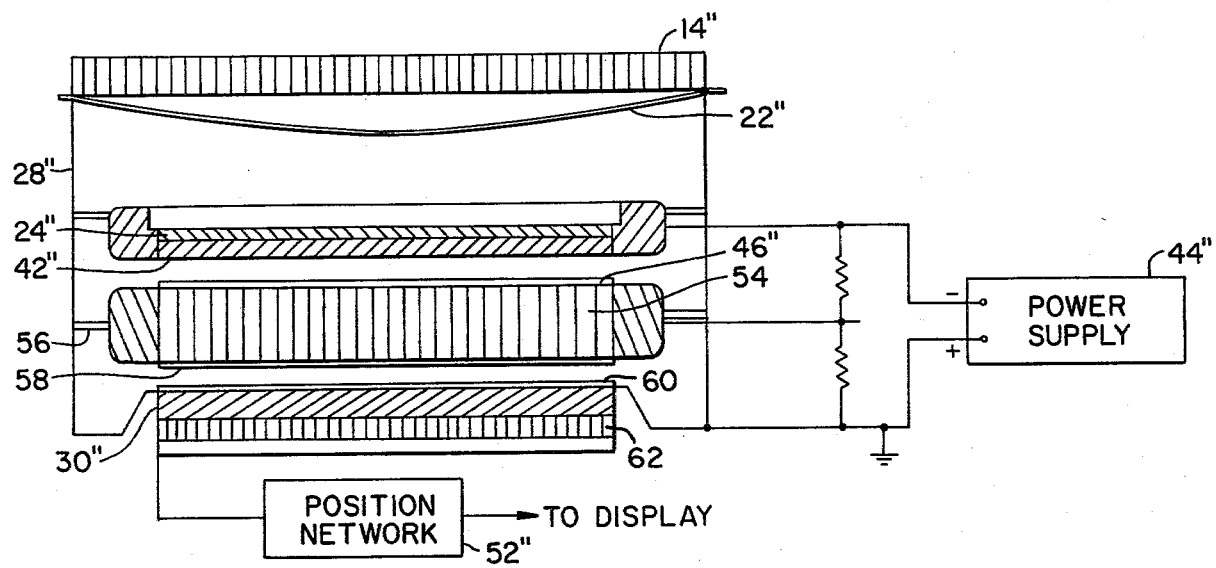
FIG._4.
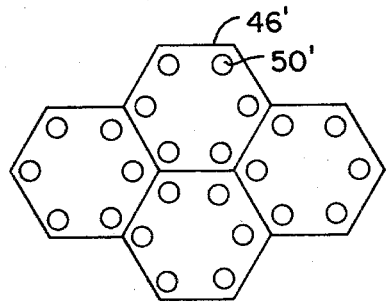
FIG._5.
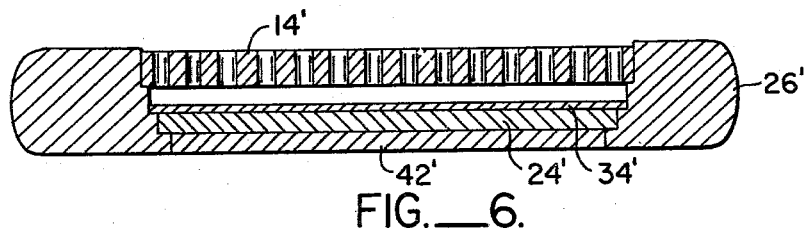
FIG._6.
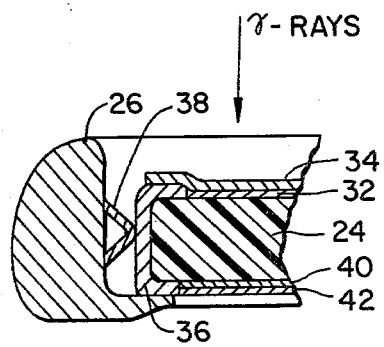
FIG._7.

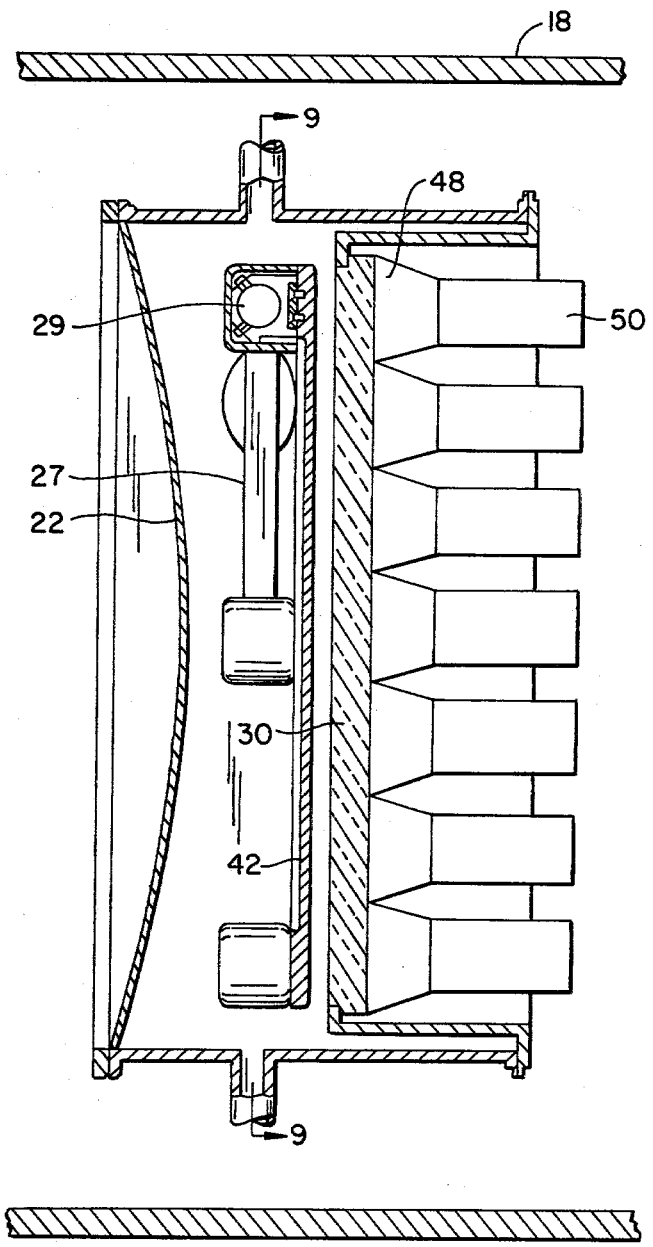
FIG._8.

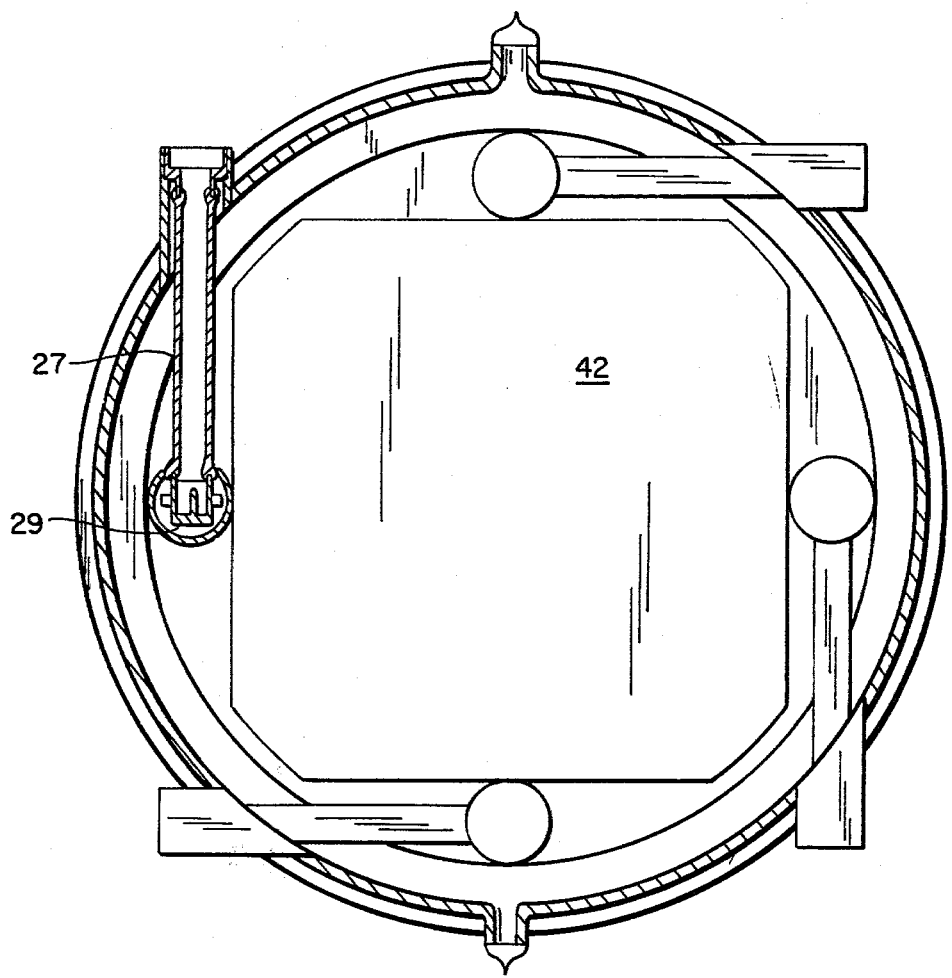
FIG.__9.
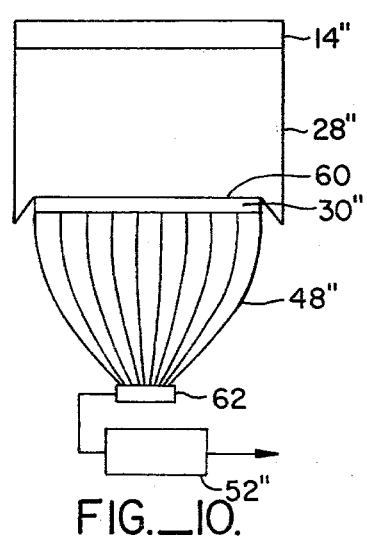
FIG.__10.

GAMMA RAY CAMERA

CROSS REFERENCE TO RELATED APPLICATION

This application is related in part to the applicant Wang's co-pending application Ser. No. 853,440, (now U.S. Pat. No. 4,140,900) filed 21 Nov. 1977, and the co-pending, joint application Ser. No. 763,638 (now U.S. Pat. No. 4,104,516) of the applicants'.

BACKGROUND OF THE INVENTION

This invention relates to radiation detectors and more particularly to scintillation cameras and radioisotope imaging devices.

A scintillation camera having a collimator, a scintillator screen, and photo-multiplier tubes (PMT) coupled to the scintillator was proposed by Hal O. Anger and is described and claimed in U.S. Pat. No. 3,011,057. In the Anger camera the photomultiplier tubes are connected to circuitry which utilizes their their signals to determine the position of each scintillation and to generate light spots or dots on the face of an oscilloscope at corresponding positions.

The Anger PMT circuitry detects both the centroid and pulse height of a gamma ray flash in the scintillator screen. The centroid location is given by x, y coordinates and the brightness or amplitude (or effective pulse height) of the flash is given by z. Therefore, the Anger camera provides the x, y, z representative characteristics of the incident gamma ray. This is done serially, that is each gamma ray flash as represented by this signal pulse at the PMT output is analyzed one by one.

The Anger camera, although widely used, has several basic limitations. These are:
 (a) Poor intrinsic spatial resolution (uncertainties in the values of x and y).
 (b) Poor pulse height resolution (uncertainties in the values of z).
 (c) Poor stability.
 (d) Poor count rate.

The basic limitations are more fully discussed below:
 (a) Intrinsic spatial resolution. The spatial resolution of the Anger camera has an extrinsic part which is related to external geometrical factors such as the objects distance from the camera, the collimator design, etc. The spatial resolution of the Anger camera also has an intrinsic part which is due to the way a gamma ray loses its energy in the scintillator and the statistics of the division of light photons from each scintillation among the PMTs and the statistics of the generation of the photoelectrons at each PMT. The intrinsic part of lower gamma ray energy levels is almost entirely due to the statistics of the division of light photons and the generations of photoelectrons at the photocathodes of the PMTs. That is, the statistics make the location of the centroid of the flash uncertain. This situation becomes worse as the gamma ray energy decreases. This is why the Anger camera cannot image low energy gamma rays very well. The spatial resolution steadily worsens at gamma ray energy levels below 500 Kev. The use of higher photocathode efficiency PMTs improves the spatial resolution somewhat. The use of more PMTs per camera also improves the spatial resolution, but it is done at the expense of stability and cost of equipment. Current camera's intrinsic spatial resolution at gamma ray energies above 200 Kev. operates at around 5 to 6 mm as measured by the full width at half maximum (FWHM) of the line distribution function, which is only marginally useful for many practical applications in nuclear medicine.

(b) Pulse height resolution. The Anger Camera's pulse height resolution is also marginal such that a large fraction of the unwanted events due to Compton scattered gamma rays are accepted as true signals. This problem worsens at lower gamma ray energies, because the energy separation between the primary gamma ray and Compton scattered gamma rays becomes smaller. The use of higher photocathode efficiency PMTs improves the pulse height resolution somewhat but not enough.

(c) Stability. Stability of the Anger camera is dependent on the gain stability of the PMTs. The more PMTs in each camera, the more control is the problem. Each one percent drift in the PMT voltage supply will cause more than 10% drift in the gain of the PMT.

(d) Count Rate. The count rate capability of the Anger camera in handling larger numbers of events in a short time period is dependent on the decay time of the thallium-activated sodium iodide NaI (T1) scintillator crystal and the dynamic response of the pulse amplifier and the pulse-shaping networks.

In various attempts to overcome one or more of the above-listed limitations of the Anger camera image intensifier tubes were introduced between the scintillator and the photodetectors. Such scintillation camera designs based on the use of image intensifier tubes are numerous and many prototype cameras have been reported. Some reports appeared even before the invention of the Anger camera. Several cameras were made available commercially but none at this day survived in the market place against the universally accepted Anger camera. The failure of these cameras can be attributed to inferior overall performance against the Anger camera. Detailed reviews of this art have been given by Muehllehner (S.P.I.E., Vol. 78, pages 113–117 (1976)) and by Moody, et al (Proc. I.E.E.E., Vol. 58, pages 217–242 (1970)). See also U.S. Pat. Nos. 3,683,185 (Muehllehner) and 3,531,651 (Lieber, et al).

There are several major shortcomings as compared to the Anger camera shared by virtually all such scintillation cameras incorporatng image intensifier tubes. These are:

(1) Poor pulse height statistics such that there is little or no ability for rejecting the Compton scattered events. This generally results in degraded image contrast and poor visibility of cold spots—rendering the camera ineffective in general use. The cause of this is either due to the inability of the design of the camera to provide pulse height analysis or due to poor collection and utilization characteristics of the visible photons from each scintillation flash in the scintillator screen.

(2) Measurable degrees of image distortion such that the camera is not able to provide a high degree of accuracy in the configuration of the image presented. This renders the camera undesirable in studies such as volumetric studies. The cause of this is due to the inherent image distorting in the inverter and minifying type image intensifier tube used and the curved scintillator screen used in the camera.

(3) Noise pulses in Image Intensifier Tubes. Noise sources which are not scintillation in origin are problems common in image intensifier tubes. For low activity gamma ray imaging, this is especially important. A common fault of the cameras in the prior art is the large number of exposed, external, negative high-voltage areas which are potential points of trouble for corona discharge and induced noise pulses.

(4) Bulk and Implosion Hazard and High Voltage Hazard. Bulk is a commonly shared problem. Inherent in the bulk is the large vacuum space enclosed in the image intensifier tubes, which is a potential hazard for implosion and scattered glass fragments.

The high voltage which must be supplied across these image intensifier tubes poses another hazard. One end of these tubes must be operated at high voltage and the other end at ground potential. The high voltage end must be properly insulated so that it will not be a shock hazard. It should also not be a noise source as mentioned above. Frequently the insulation is so thick as the photocathode end that the collimator can not be placed close enough to the scintillator screen to minimize the extrinsic spatial resolution loss for the camera to take advantage of the gained intrinsic spatial resolution.

The closest prior art to the present invention are disclosed in U.S. Pat. No. 3,683,185 (Muehllehner) and U.S. Pat. No. 3,531,651 (Lieber, et al). The Muehllehner camera consists of a flat crystal scintillator screen external to a large diameter image intensifier tube of the electrostatic inverter with minified output design with a curved input photocathode surface, two additional tubes of the electrostatic inverter type design all with a curved input photocathode and curved output phosphor, and a positional sensing detector and circuit. In one of the Muehllehner embodiments and in the Lieber, et al patent are also disclosed designs with a curved scintillator screen inside the image intensifier tube and curved photocathode deposited on the screen. All of these cameras suffer at least the faults discussed at paragraphs 2, 3 and 4 above.

The electrostatic inverter type of image intensifier tubes introduce a substantial amount of spatial distortion making accurate volumetric determination with this camera doubtful. The high voltage must be supplied to the input end making insulation and placement of the collimator difficult. The placement of the scintillator screen outside of the tube causes inefficient optical coupling to the photocathode and in turn causes poor pulse height resolution and poor spatial resolution. Neither Muehllehner, nor Lieber, et al, show how the internal crystal scintillator can be properly used and coupled to the photocathode.

SUMMARY OF THE INVENTION

The above and other disadvantages of prior art image intensifier gamma ray cameras are overcome by the present invention of a modified Anger camera comprising a collimator, a flat scintillator screen aligned with the collimator, a first flat photocathode disposed with its flat surfaces parallel and adjacent to the scintillator screen, a first flat output phosphor display screen which is spaced apart from and parallel to the photocathode and on its side opposite from the scintillator screen, an output window upon which the first display screen is mounted, a metallic input window, an open-ended, hollow metallic tube envelope surrounding to the scintillator screen and the photocathode and which is closed at one end by the output window and at the other end by the input window and which is evacuated, and means for applying an accelerating electrostatic potential between the display screen and the photocathode. The collimator is located exterior to the tube envelope in one embodiment and is spaced closely adjacent to the input window. In another embodiment the collimator is mounted within the tube envelope and ahead of the scintillator screen, taken in the direction of the impinging radiation.

In the preferred embodiment of the invention the scintillation screen, the photocathode and the output display screen have substantially the same diagonal dimensions. A plurality of photo-detectors are optically coupled to the output display screen through the output window. These photo-detectors, such as photo-multiplier tubes, are connected to conventional Anger camera circuitry which processes the signals emanating from the photo-multipier tubes, and produces an image corresponding to the light image generated by the incident radiation on the scintillator. The generation of this image is substantially the same as is done in the Anger U.S. Pat. No. 3,011,057, however, because of the increased conversion efficiency of the image intensifier tube of the invention and because the scintillator's crystal is located immediately adjacent to the photocathode layer, greater pulse height statistics and thus greater spatial resolution are achieved.

In the preferred embodiment of the invention each incident gamma ray photon produces a multitude of photons at the output display screen which can be accurately triangulated by the photo-multiplier tubes. This also allows the photo-multiplier tube circuit to easily discriminate between direct, incident radiation and scattered radiation.

In a modification of the preferred embodiment the scintillator screen, the photocathode and the output display screen are segmented and the circuitry associated with the photo-multiplier tubes of the various segments operate independently from each other so that each segment operates as a separate gamma ray camera.

In still another embodiment of the invention a second stage of amplification is introduced. In this two stage version of the invention the first output display screen is mounted on one side of a fiber optic plate rather than on the output window. A second photocathode is mounted on the opposite side of the fiber optic plate. A second output display screen is mounted on the output window and is spaced apart and parallel to the second photocathode. Additional means are utilized for applying electrostatic potential between the second photocathode and a second output display screen. This arrangement gives even greater capability for detecting between direct and scattered radiation.

In all of the above-described embodiments the input window is metallic and is preferably made of Type 17-7 PH stainless steel. This steel has been found to have highly desirable x-ray input characteristics as more fully described in the applicant's co-pending application Ser. No. 853,440, filed Nov. 21, 1977, now U.S. Pat. No. 4,140,900. The essentially all metallic and rugged construction of the tube minimizes the danger of implosion. The small vacuum space enclosed by the tube represents much smaller stored potential energy as compared with a conventional tube which further minimizes implosion danger. Furthermore, if punctured, the metal behaves differently from glass and the air simply leaks in without fracturing or imploding.

It is therefore an object of the present invention to provide an improved Anger type gamma ray camera utilizing a proximity type image intensifier tube;

It is still another object of the present invention to provide an improved Anger type gamma ray camera having greater capability for distinguishing between incident and scattered radiation.

It is a still further object of the invention to provide an improved Anger type gamma-ray camera having greater spatial resolution capabilities.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 1 is a diagrammatic vertical, sectional view, with portions broken away of the gamma ray camera according to the invention;

FIGS. 2 and 3 are graphical illustrations for use in describing the invention;

FIG. 4 is a diagrammatic illustration of a second, two stage embodiment of the invention;

FIG. 5 is a plan view of the output display screen of still another modified embodiment of the invention;

FIG. 6 is a vertical, sectional view of a combined collimator-scintillator screen assembly of still another embodiment of the invention;

FIG. 7 is an enlarged, vertical sectional view of a detail of the scintillator screen assembly of the embodiment shown in FIG. 1.

FIG. 8 is a detailed sectional view, in section, of the image intensifier tube of the invention;

FIG. 9 is a vertical, sectional view, taken generally along the line 9—9 in FIG. 8, of the image intensifier tube according to the invention; and FIG. 10 is a diagrammatic view of a modification of the embodiment depicted in FIG. 4.

DESCRIPTION OF CERTAIN PREFERRED EMBODIMENTS

Referring now more particularly to FIG. 1, the gamma ray camera according to the invention is illustrated. In this simplified diagram, a radiation emitting body 10, such as a human patient containing a small amount of radioactive isotope, emits radiation stimuli 12 in terms of gamma ray photons which impinge on a parallel hole collimator 14. The collimator is made of a high atomic number material such as lead, tungsten or tantalum which stops the gamma rays 12 except where a through hole 16 is provided.

The collimator is mounted at one end of a casing 18 which surrounds the camera 20 of the invention. Behind the collimator 14, with respect to the direction of travel of the gamma rays 12, is mounted an image intensifying tube. The image intensifier tube comprises a metallic, typically type 304 stainless steel, vacuum tube envelope 28 and a metallic, inwardly concave input window 22 immediately adjacent to the collimator 14. The window 22 is made of a specially chosen metal foil or alloy metal foil in the family of iron, chromium, and nickel, and in some embodiments, additionally combinations of iron or nickel together with cobalt or vanadium. It is important to note that these elements are not customarily recognized in the field as good gamma ray transmitting window materials in diagnostic devices. By making the window thin, down to 0.1 mm in thickness, the applicant was able to achieve high gamma ray transmission with these materials and at the same time obtain the desired tensile strength. In particular, a foil made of 17-7 PH type of precipitation hardened chromium-nickel stainless steel is utilized in the preferred embodiment. This alloy is vacuum tight, high in tensile strength and has very attractive gamma ray transmission properties: high transmission to primary gamma rays, low self-scattering, and reasonably absorbing with respect to Compton scattered gamma rays. The window 22 is concaved into the tube like a drum head.

The use of materials which are known for high gamma transmission such as beryllium, aluminum and titanium for example cause undesirable scattering.

One purpose of having a metallic window 22 is that it can be quite large in diameter with respect to the prior art type of convex, glass window, without affecting the image quality. In one embodiment, the window measures 0.1 mm thick, 25 cm by 25 cm and can withstand over 100 pounds per square inch of pressure. The input window can be square, rectangular, or circular in shape, since it is a high tensile strength material and is under tension rather than compression.

Behind the input window 22, again taken in the direction of travel of the gamma ray radiation 12, is the scintillation screen 24. This scintillation screen is mounted in a corona shield and support ring 26 which, in turn, is mounted in the metallic tube envelope 28. The envelope 28 is closed at the front end by the input window 22 and at the opposite end by a glass output window 30. On the side of the scintillation screen 24 closest to the input window 22 is a reflective back 32 and on top of that is a metallized support layer 34.

Referring now more particularly to FIG. 7, the detailed construction of the scintillator-photocathode screen assembly is illustrated. In the enlarged detailed view of FIG. 7, it can be seen that the screen 24, which is shown as a single crystal slab, is provided with a metallized edge 36 which is in electrical contact with a spring 38 mounted in the corona shield and support ring 26. The flat face of the crystal 24 opposite from the metallized layer 34 and the reflective layer 32 is optionally covered with a barrier layer 40 of freshly vapor deposited CsI (Na), CsI, bismuth germanate, or $Al_2O_3$ which all have similar indexes of refraction. On top of this layer 40 is deposited the photocathode layer 42, which is in electrical contact with the metallized edge 36.

Examples of appropriate materials to be used in this screen assembly are aluminum, aluminum oxide or titanium oxide for the reflecting layer 32, aluminum or chromium for the metallized layer 34 and CsI(Na) for the crystal 24. The layers 32 and 34 may be vapor deposited. The layers 32, 34 and 40 are typically thicker than 0.1 m and thinner than 25μ. The crystal 24 can also be made of NaI(Tl). For equivalent gamma ray stopping power, a crystal made of CsI(Na) can be made thinner than NaI(Tl), however, for better pulse-height statistics NaI(Tl) is used. The crystal can be vapor deposited on the reflective coating 32 and metallized substrate 34. The crystal can also be a single crystal slab.

When the crystal 24 is a single crystal slab cut from a single crystal ingot, and if the thickness is of the order of 1 to 2 mm or thicker, it may not be necessary to use the metallized substrate 34 for mechanical support. Since there is usually extensive handling of the crystal slab prior to the tube assembly, a thin layer of freshly (just prior to final tube assembly) vapor deposited CsI(Na), bismuth germanate, CsI or $Al_2O_3$ as a barrier layer 40 on the scintillator screen is desirable. The purpose of the layer is to prevent the photocathode from being poisoned by surface impurities on the crystal. This barrier layer is especially important in the case of NaI(Tl) crystal 24 where the barrier layer is also used to minimize the vaporization or escape of TlI. However, it is important to point out here that it is also the object of this invention that the visible photons from each scintillation are efficiently collected by the photocathode. This is achieved through the use of barrier layer materials which have a matching index of refraction with the scintillation crystal.

Another transparent and conductive layer may be introduced between the barrier layer 40 and the photocathode 42 to provide improved electrical conductivity and surface cleanliness. Materials such as Ti or Ni metal may be used for this purpose.

The photocathode layer 42 can be $Cs_3Sb$, that is industry phosphor types S-9 or S-11. Fabrication methods for this photocathode layer are well known. The applicant has found good success with the pre-evaporated antimony method—a thin layer of antimony is deposited on the scintillation screen 24 prior to the assembly of the tube and exhaust bake cycle, and cesium vapor is introduced after the exhaust bake cycle and at a processing temperature of 120° to 170° C. Higher efficiency photocathodes such as multi-alkali antimonide can also be used. $(KCs)_3Sb$, commonly known as bi-alkali photocathode, can also be used. The applicant found that $(KCs)_3Sb$ can also be deposited with the pre-evaporated antimony method—introduction of potassium vapor is followed by the introduction of cesium vapor and the photocathode 42, with a negative high potential. The remaining parts of the intensification tube including the metallic envelope 28, are all operated at ground potential. This concept of minimizing the surface area which is negative with respect to the output screen results in reduced field emission rate inside the tube and allows the tube to be operable at higher voltages and thus higher brightness gain. As previously mentioned above, reducing field emissions is especially desirable in a gamma ray camera because of the relatively low rate of occurrence of incident stimuli. It also minimizes the danger of electrical shock to the patient or workers if one should somehow come in contact with the exterior envelope of the tube.

The thick, high atomic number (Z) glass substrate 30 on which the phosphor display screen 46 is deposited and which forms one exterior end wall of the vacuum tube envelope 28, is attached to the tube envelope 28 by means of a collar 31 made of an iron, nickel, chromium alloy, designated to the trade as "Carpenter, No. 456". Since the thermal coefficient of expansion of this alloy matches that of the glass and nearly matches that of the tube envelope 28, the collar 31 can be fritted to the glass substrate 30 and welded to the tube envelope 28. The thickness of the scintillator screen 24 is in the range of 0.5 mm. to 50 mm. for a gamma ray energy range of 30 Kev to 511 Kev.

The corona shield and support ring 26 is made of aluminum, with an aluminum oxide coating ($Al_2O_3$), and supports the scintillator screen 24. This ring is in electrical contact with the screen 24 and the photocathode 42 which is deposited on the screen 24. The ring 26 is supported from the metal tube envelope 28 on insulators 27 (see FIGS. 8 and 9) and is connected to a high voltage power supply 44. The high voltage power supply 44 is also connected to the tube envelope 28 which is electrically connected to an output phosphor screen 46 deposited on the interior flat surface of the output window 30. The ground terminal of the supply 44 is connected to the envelope 28 so that no shock potential exists to the operator of the equipment.

As mentioned above, the corona shield and support ring 26 for the scintillator and photocathode in this invention is suspended from the tube envelope 28 between the input window 22 and the output screen 46 by the several insulating posts 27. One or more of these posts may be hollow in the center to allow an insulated high voltage cable 29 from the source 44 to be inserted to provide the scintillator 24 with high voltage.

To reduce charges accumulated on the insulating posts 27, they are coated with a slightly conductive material such as chrome oxide which bleeds off the accumulated charge by providing a leakage path of better than 20 Kv/cm.

The output phosphor screen 46 can be made of well known phosphor types P-15 or P-16 with the standard thin aluminum film coating on the vacuum side. These phosphors are considered relatively fast in their response time. This fast response is needed when each individual gamma ray scintillation flash is examined serially on a one by one basis by both its flash brightness (pulse height) on the output screen 46 and by the centroid or the weighted average location of the flash on the screen.

Optically coupled to the exterior flat surface of the output window 30 by means of light guides 48 are a plurality of photo-multiplier tubes 50. These tubes, in turn, are connected to a triangulation and pulse height analyzing circuit 52. The arrangement of the photo-multiplier tubes 50 and the circuitry of the position locating or triangulation and pulse height analyzing network 52 are well known to those skilled in the art and in particular are described with reference to FIG. 2 in Anger U.S. Pat. No. 3,011,057 or with reference to FIGS. 5 and 6 of Muehllehner U.S. Pat. No. 3,683,185 and hence will not be described in greater detail here. The output of the position network 52 is supplied to an appropriate display such as a cathode ray tube oscilloscope 54. The pulse height selection of the display as well as the x and y coordinates of the display are controlled by the position network 52 as is more fully described in the Anger U.S. Pat. No. 3,011,057 and the Muehllehner U.S. Pat. No. 3,683,185.

In operation, the gamma rays 12 from the body 10 pass through the holes 16 of the collimator 14 and impinge on the scintillator screen 24, thereby producing a localized flash of light. This flash of light causes the photocathode 42 to produce a corresponding pattern of photoelectrons which are accelerated to the output screen 46 by means of the electrostatic potential between the photocathode 42 and the output screen 46 which is supplied by the high voltage supply 44. The accelerated photoelectrons which impinge on the phosphor output screen 46 produce corresponding light flashes on the output screen whih are detected by the photo-multiplier tubes 50.

The parallel-hole collimator 14 can also be replaced for certain applications by several other well-known types of collimators such as: pin-hole, diverging hole, converging hole, etc. Design considerations of these collimators are also well known. See, for example, the following articles:

(1) E. L. Keller, J. Nuc. Med. Vol 9, pages 233–235 (1968) "Optimum Dimensions of parallel-hole multi-aperture collimators for Gamma-ray Cameras".

(2) H. O. Anger, "Radioisotope Cameras" in Instrumentation in Nuclear Medicine, ed. Gr. J. Hines (Academic Press 1967) pages 485–552.

The design considerations of the light guide 48 are also well known. See for example U.S. Pat. Nos. 3,683,180 and 3,011,057.

As mentioned at the beginning of this description, the use of the image intensifier structure between the photomultiplier tubes 50 and the scintillator crystal 24 greatly increases the number of photons produced with each incident gamma ray thereby greatly increasing the ability of the triangulation network 52 to locate the centroid of the flash and to further allow the network to better distinguish between incident and scattered gamma rays by means of improved pulse height statistics. The increase in the number of photons is referred to as the pulse gain. The relationship between the pulse gain and image intensification tube voltage is shown in FIG. 2 for a typical combination of S11 (Cs-Sb) kind of photocathode and P15 type of output phosphor.

For the same reason, the camera according to the invention is able to operate satisfactorily at lower gamma ray energy levels than a conventional Anger camera, as is illustrated in FIG. 3. Thus, the camera of the invention greatly improves the performance of a conventional Anger camera without introducing any other disadvantages as most prior art systems do. This improvement is obtained through the selection of a flat scintillator screen, a flat photocathode layer efficiently coupled to the scintillation screen, a flat output screen, and an image intensification apparatus having extremely good pulse height statistics.

Referring now more particularly to FIG. 5, a modified embodiment of the camera of the invention is described. In the conventional Anger camera as well as the modified and improved Anger camera described above, the outputs from the photo-multiplier tubes 50 are processed serially. This puts a limitation on the response time of the camera. In order to increase the system count rate, and hence its response, the scintillator screen 24, the photocathode 42, and the output screen 46 can be segmented in corresponding and aligned segments. The segmentation of the output screen is illustrated in FIG. 5 by the reference numeral 46' and it is to be understood that the segmentations of the scintillator crystal 24 and the photocathode layer 42 are similarly segmented and aligned. The photo-multiplier tubes 50 can be arranged in a pattern as shown by the reference numeral 50' for each segment. The triangulation network 52 is then arranged to process the outputs of the photo-multiplier tubes 50' serially only within a given segment. The outputs from the tubes in the other segments are also processed at the same time. The outputs from the position network 52 may be sampled serially for purposes of display or they may be supplied simultaneously to a multiple trace display. In this modification of the basic gamma ray camera according to the invention, the segmentations are optically partitioned to prevent cross-talk.

It is important to place the scintillator crystal 24 as close to the collimator 14 as possible so that the high spatial resolution of the camera can be utilized. A substantial space between the collimator and the input screen causes deterioration in the system's spatial resolution characteristics. The input screen in the basic camera should be placed as close to the input window 22 as possible without causing high voltage problems due to too close a proximity. A better approach, however, is illustrated in FIG. 6, in which a modified collimator 14' is within the tube envelope 28, supported in the corona and support ring 26' on the side of the scintillator crystal 24' which faces the object 10. It should be noted that elements corresponding to those described above have been given the corresponding reference numerals primed.

Referring now more particularly to FIG. 4, a modified camera according to the invention which allows the use of low cost solid state photo-detectors in place of the photomultiplier tubes 50, is illustrated. In this embodiment, there are two output phosphor display screens and two photocathodes. Corresponding elements have been given the same numerals, double primed.

The first output phosphor display screen 46" is mounted on one face of a fiber-optic plate 54 which is suspended from the tube envelope 28" by means of insulators 56. On the opposite face of the fiber-optic plate 54 a second photocathode 58 is deposited. The first and second photocathodes 46" and 58 can be of the same material as described above for the primary embodiment of the invention. The fiber-optic plate 54 is oriented in a plane parallel to the first scintillator crystal 24".

A second output phosphor display screen 60 is deposited on the output window 30". The power supply 44" is connected between the first output phosphor display screen 46" and the first photocathode 42" as well as between the second photocathode 58 and the second output phospher display screen 60. The power supply is biased such that the potential between the first photocathode screen 42" and the first output display screen 46" is approximately equal to the potential between the second photocathode 58 and the second output display screen 60. The potential between the first photocathode and the second output phosphor display screen 60 is double these intermediate potentials. The first output display screen 46" and the second photocathode 58 are connected together to have the same potential.

In place of the photo-multiplier tubes at the output display screen is an array of solid state detectors 62 which are coupled to a position network 52". These solid state detectors sense the light output image at the second output display screen in the same way that the photo-multiplier tubes operated in the embodiment depicted in FIG. 1. See for example U.S. Pat. No. 3,683,185 (Muehllehner). The output from the position network 52" is supplied to an appropriate display as in the primary embodiment. Appropriate light guide 48" is placed between the detector array 52 and the output window 46". The great advantage offered by the two stages of amplification in this embodiment is the use of the simpler solid state detectors in place of the photomultiplier tubes. These solid state detectors are simpler, more stable and far less expensive than the photo-multiplier tubes.

Another embodiment is a converging array of light guides 48''', as shown in FIG. 10, coupling to the above described Z-stage tube on one end and on the other end to a smaller array of solid state detectors. For more efficient transfer of light, each light guide may be claded with low index of refraction material.

From the foregoing description, it can be seen that the conventional Anger camera has been modified by the applicant's interposition of a proximity type image intensifier tube between the scintillator screen and the photo-detector network so that the camera can operate at better spatial resolution and with better scatter rejection at lower gamma ray energy ranges.

It should also be pointed out that there has heretofore been a common misconception about the one-to-one type of image size image intensifier approach taken in the present invention. That is the concept of gain. Normally, the gain of a tube is defined by the brightness gain which is the product of the true electronic gain of the tube and the gain obtained through minification of the output image. Since a one-to-one type image intensifier tube does not minify the output image, its brightness gain is the same as the true electronic gain, whereas an electrostatic inverter type of tube with a 10X minified output image would have a brightness gain 100X higher than that of the one-to-one type. However, in applications where pulse counting and sensing are used, only the true electronic gain is of value. Gain obtained through minified output is of no value. Thus, the false fear of not enough gain in a one-to-one design discouraged prior attempts of the foregoing approach.

While in the above description it has been assumed that the incident radiation are gamma rays in other less preferred embodiments the radiation can be other types of nuclear radiation such as protons.

The terms and expressions which have been employed here are used as terms of description and not of limitation, and there is no intention, in the use of such terms and expressions, of excluding equivalents of the features shown and described, or portions thereof, it being recognized that various modifications are possible within the scope of the invention claimed.

What is claimed is:

1. An improved scintillation camera of the type having a radiation collimator, scintillator means aligned with the collimator for converting radiation passing through the collimator and impinging upon the scintillator means into a corresponding light pattern, the scintillator means including a scintillator screen and an output screen for displaying the light patterns, a plurality of photo-electric detectors disposed in view of substantially co-extensive portions of the output screen, and means connected to the photo-electric detectors for receiving signals emitted from them and for translating such signals into relatively displaced images of said light patterns, wherein the improvement resides in the scintillator means which comprise:
    a flat scintillator screen,
    a first flat photocathode disposed with its flat surfaces parallel to and adjacent to the scintillator screen,
    a first flat output phosphor display screen which constitutes the light output screen of the scintillator means, the display screen having its flat surfaces parallel to and spaced apart from the flat surfaces of the photocathode and on its side opposite from the scintillator screen,
    an output window on which the display screen is mounted,
    a metallic input window,
    means for applying an accelerating electrostatic potential between the display screen and the photocathode, and
    an open ended, hollow, evacuated envelope surrounding the scintillator screen and the photocathode and which is closed at one end by the output window and at the other end by the input window.

2. An improved scintillation camera as recited in claim 1 wherein the envelope is metal and the electrostatic potential means supply a high negative potential to the scintillator screen and photocathode and a ground potential to the output display screen and the envelope.

3. An improved scintillation camera as recited in claim 1 wherein the scintillation screen, the photocathode and the output display screen have substantially the same diagonal dimensions.

4. An improved scintillation camera as recited in claim 1 further comprising separate, converging light guides for coupling the photo-electric detectors to the output window.

5. An improved scintillation camera as recited in claim 1 wherein the input window is concave inwardly with respect to the tube envelope and is made from type 17-7 PH stainless steel.

6. An improved scintillation camera as recited in claim 1 wherein the scintillator screen is a scintillator crystal and further comprising a thin layer of light transmitting material interposed between the photocathode and the scintillator crystal which material has an index of refraction which matches the index of refraction of the scintillator crystal.

7. An improved scintillation camera as recited in claim 6 wherein the thin layer is comprised of freshly vapor deposited CsI.

8. An improved scintillation camera as recited in claim 6 wherein the thin layer is comprised of freshly vapor deposited CsI(Na).

9. An improved scintillation camera as recited in claim 6 wherein the thin layer is comprised of $Al_2O_3$.

10. An improved scintillation camera as recited in claim 1 further comprising a fiber optic plate, a second photocathode and a second output phosphor display screen and wherein the first output display screen is mounted on one side of the fiber optic plate and the second photocathode is mounted on the other side of the fiber optic plate, the second output display screen being spaced apart from the second photocathode and plane parallel to it, means for applying an accelerating electrostatic potential between the second photocathode and the second ouput display screen and wherein the second photocathode, the fiber optic plate and the second output display screen are contained within the tube envelope.

11. An improved scintillation camera as recited in claim 1 wherein the scintillator screen, the first photocathode, the first output display screen and the output window are divided into optically isolated segments and wherein the signal translating means connected to the photodetectors of different segments are operated simultaneously, each of the photodetectors associated with a given segment being sampled serially.

12. An improved scintillation camera as recited in claim 1 wherein the collimator is mounted within the tube envelope and adjacent to the scintillator screen.

13. A scintillation camera comprising a radiation collimator, a flat scintillator screen aligned with the collimator for converting radiation passing through the collimator and impinging upon the scintillator screen into a corresponding light pattern,
    a first flat photocathode disposed with its flat surfaces parallel to and adjacent to the scintillator screen for converting the light patterns on the scintillator screen into corresponding patterns of emitted photo-electrons,
    a first flat output phosphor display screen, the display screen having its flat surfaces parallel to and spaced apart from the flat surfaces of the photocathode and on its side opposite from the scintillator screen, the scintillator screen, the photocathode and the output phosphor display screen all having the same diagonal dimensions, an output window on which the display screen is mounted, means for applying an accelerating, negative electrostatic potential between the photocathode and the display screen to accelerate the photo-electrons emitted by the photocathode toward the output phosphor display screen where they impinge upon it and produce corresponding, intensified light spots which form a pattern, a plurality of photo-electric detectors disposed in view of substantially co-extensive portions of the output screen, and resolving means connected to the photo-electric detectors for receiving signals emitted from them and for analyzing the pulse heights of the signals and for locating the relative positions of the light spots on the display screen, an input window, and an open ended, hollow, evacuated tube envelope surrounding the scintillator screen and the photocathode and which is closed at one end by the output window and at the other end by the input window.

14. A scintillation camera as recited in claim 13 wherein the input window is concave inwardly with respect to the tube envelope and is made from type 17-7 PH stainless steel.

15. A scintillation camera as recited in claim 13 further comprising a fiber optic plate, a second photocathode and a second output phosphor display screen and wherein the first output display screen is mounted on one side of the fiber optic plate and the second photocathode is mounted on the other side of the fiber optic plate, the second output display screen being spaced apart from the second photocathode and plane parallel to it, means for applying an accelerating electrostatic potential between the second photocathode and the second output display screen and wherein the second photocathode, the fiber optic plate and the second output display screen are contained within the tube envelope.

16. A scintillation camera as recited in claim 13 wherein the scintillator screen, the first photocathode, the first output display screen and the output window are divided into optically isolated segments and wherein the signal translating means connected to the photodetectors of different segments are operated simultaneously, each of the photodetectors associated with a given segment being sampled serially.

17. A scintillation camera as recited in claim 13 wherein the collimator is mounted within the tube envelope and adjacent to the scintillator screen.

18. A scintillation camera as recited in claim 13 wherein the scintillator screen is a scintillator crystal selected from the group consisting essentially of CsI(Na) or NaI(Tl) and further comprising a barrier layer interposed between the scintillator crystal and the photocathode, the barrier layer being transparent and having an index of refraction which matches the index of refraction of the scintillator crystal.

19. A scintillation camera as recited in claim 18 wherein the barrier layer is made of a material selected from the group consisting essentially of CsI(Na), CsI, bismuth germanate or $Al_2O_3$.

20. An improved scintillation camera of the type having a radiation collimator, a scintillator aligned with the collimator for converting radiation passing through the collimator and impinging upon the scintillator into corresponding light spots which form a pattern, the scintillator including an output screen for displaying the light spots, a plurality of photoelectric detectors disposed in view of substantially co-extensive portions of the output screen, and resolving means connected to the photo-electric detectors for receiving signals emitted from them and for resolving such signals into coordinate electric signals corresponding to the position coordinates of the light spots on the display screen, wherein the improvement comprises:

a flat scintillator screen, a first flat photocathode disposed with its flat surfaces parallel to and adjacent to the scintillator screen, a first flat output phosphor display screen which constitutes the light output screen of the scintillator, the display screen having its flat surfaces parallel to and spaced apart from the flat surfaces of the photocathode and on its side opposite from the scintillator screen, an output window on which the display screen is mounted, a metallic input window, means for applying an accelerating electrostatic potential between the display screen and the photocathode, and an evacuated envelope surrounding the scintillator screen and the photocathode and which is closed at one end by the output window and at the other end by the input window.

21. An improved scintillation camera as recited in claim 20 wherein the resolving means include a pulse height discriminator circuit to distinguish between incident and scattered radiation rays.

* * * * *